United States Patent
Kucmierczyk et al.

(10) Patent No.: US 12,006,287 B2
(45) Date of Patent: Jun. 11, 2024

(54) PROCESS FOR ALKOXYCARBONYLATION OF ETHYLENICALLY UNSATURATED COMPOUNDS USING BENZENE-BASED DIPHOSPHINE LIGANDS AND ALUMINIUM TRIFLATE

(71) Applicant: EVONIK OPERATIONS GMBH, Essen (DE)

(72) Inventors: Peter Kucmierczyk, Herne (DE); Ricarda Dühren, Rostock (DE); Dirk Fridag, Haltern am See (DE); Johannes Knossalla, Gahlen (DE); Anna Chiara Sale, Recklinghausen (DE); Ana Markovic, Haltern am See (DE); Alexander Brächer, Haltern am See (DE); Matthias Beller, Ostseebad Nienhagen (DE); Robert Franke, Marl (DE)

(73) Assignee: EVONIK OXENO GMBH & CO. KG, Marl (DE)

( * ) Notice: Subject to any disclaimer, the term of this patent is extended or adjusted under 35 U.S.C. 154(b) by 53 days.

(21) Appl. No.: 17/530,720

(22) Filed: Nov. 19, 2021

(65) Prior Publication Data

US 2022/0162150 A1    May 26, 2022

(30) Foreign Application Priority Data

Nov. 24, 2020 (EP) .................................... 20209477

(51) Int. Cl.
*C07C 67/38* (2006.01)
*B01J 31/02* (2006.01)
*B01J 31/22* (2006.01)

(52) U.S. Cl.
CPC .......... *C07C 67/38* (2013.01); *B01J 31/0267* (2013.01); *B01J 31/2239* (2013.01); *B01J 2531/0208* (2013.01); *B01J 2531/824* (2013.01)

(58) Field of Classification Search
CPC .......... B01J 2531/0208; B01J 2531/824; B01J 31/0267; B01J 31/2239; C07C 67/38; C07C 69/24; G01K 13/00; G01K 7/04; G01K 7/18; G01K 7/22; H01G 11/08; H01G 11/18; H01G 11/24; H01G 11/62; H01G 11/84; H01G 9/14; H01M 10/0525; H01M 10/443; H01M 10/615; H01M 10/63; H01M 10/637; H02J 2207/50; H02J 7/0047; H02J 7/345; H05B 1/023; H05B 3/0004; H05B 3/0014; H05B 3/03; Y02E 60/10; Y02T 10/70

See application file for complete search history.

(56) References Cited

U.S. PATENT DOCUMENTS

| | | | |
|---|---|---|---|
| 9,688,604 B2 | 6/2017 | Jennerjahn et al. | |
| 9,725,398 B2* | 8/2017 | Dong | C07C 67/38 |
| 10,077,228 B2 | 9/2018 | Dong et al. | |
| 10,202,329 B2 | 2/2019 | Dong et al. | |
| 10,294,191 B2 | 5/2019 | Dong et al. | |
| 2018/0022686 A1* | 1/2018 | Fang | B01J 27/13 |
| | | | 560/232 |
| 2020/0392064 A1 | 12/2020 | Kumierczyk et al. | |

FOREIGN PATENT DOCUMENTS

| | | | |
|---|---|---|---|
| EP | 3 121 184 A2 | 1/2017 | |
| EP | 3 750 620 A1 | 12/2020 | |

OTHER PUBLICATIONS

Millar (Tips and Tricks for the Lab: Air-Sensitive Techniques (2), 11 pages, Published 2013) (Year: 2013).*
Williams et al. (Aluminum Triflate as a Highly Active and Efficient Nonprotic Cocatalyst in the Paladium-Catalyzed Methoxycarbonylation Reaction, Comm. Angew. Chem. Int. Ed. 47, pp. 560-563, Published 2008) (Year: 2008).*
European Search Report dated May 18, 2021 for European Patent Application No. 20209477.7 (8 pages in German with Machine Translation).
Dong, K., et al. Efficient Palladium-Catalyzed Alkoxycarbonylation of Bulk Industrial Olefins Using Ferrocenyl Phosphine Ligands. 2017. Agnewandte Chemie International Edition. vol. 56, pp. 5267-5271.
Williams, D. B. G., et al. Aluminum Triflate as a Highly Active and Efficient Nonprotic Cocatalyst in the Palladium-Catalyzed Methoxycarbonylation Reaction. Agnewandte Chemie International Edition. 2008. vol. 47, pp. 560-563.

* cited by examiner

*Primary Examiner* — Jafar F Parsa
*Assistant Examiner* — Blaine G Doletski
(74) *Attorney, Agent, or Firm* — Smith, Gambrell & Russell, LLP

(57) ABSTRACT

Process for alkoxycarbonylation of ethylenically unsaturated compounds using benzene-based diphosphine ligands and aluminium triflate.

9 Claims, No Drawings

PROCESS FOR ALKOXYCARBONYLATION OF ETHYLENICALLY UNSATURATED COMPOUNDS USING BENZENE-BASED DIPHOSPHINE LIGANDS AND ALUMINIUM TRIFLATE

The invention relates to a process for alkoxycarbonylation of ethylenically unsaturated compounds using benzene-based diphosphine ligands and aluminium triflate.

The alkoxycarbonylation: of ethylenically unsaturated compounds is a process of increasing significance. An alkoxycarbonylation is understood to mean the reaction of ethylenically unsaturated compounds (olefins) with carbon monoxide and alcohols in the presence of a metal-ligand complex to give the corresponding esters. Typically, the metal used is palladium.

The following scheme shows the general reaction equation of an alkoxycarbonylation:

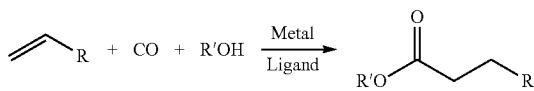

EP 3 121 184 A2 describes a process for alkoxycarbonylation of olefins using benzene-based diphosphine compounds. A BrØnsted acid was added here to each reaction: para-toluenesulfonic acid (PISA), trifluoromethanesulfonic acid or sulfuric acid.

However, sulfuric acid causes severe corrosion to metallic surfaces. A further disadvantage that the use of sulfuric acid entails is that it has to be pretreated/degassed in a complex manner.

Catalyst systems are frequently sensitive to oxygen. Contact even with traces of oxygen leads to oxidation of the ligand, which ultimately leads to a decrease in the activity of the overall catalyst complex. Traces of oxygen can be introduced by entrainment, for example, via the continuous introduction of components.

The technical problem addressed by the invention is that of providing a novel process that does not have the disadvantages associated with the use of the BrØnsted acid known from the prior art. In addition, the process is to give a good yield.

The object is achieved by a process according to Claim 1.

Process comprising the process steps of:

a) initially charging an ethylenically unsaturated compound;

b) adding a ligand of formula (I):

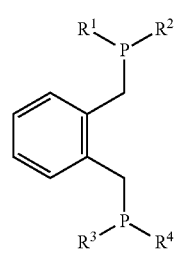

where
$R^1$ and $R^3$ are each a $-(C_3-C_{20})$-heteroaryl radical,
$R^2$ and $R^4$ are each $-(C_1-C_{12})$-alkyl,
and a compound comprising Pd;

c) pretreating aluminium triflate by applying reduced pressure;

d) adding the pretreated aluminium triflate from c), where the ratio of aluminium triflate:ligand is in the range from 2 mol:1 mol to 25 mol:1 mol;

e) adding an alcohol;

f) feeding in CO;

g) heating the reaction mixture from a) to f), with conversion of the ethylenically unsaturated compound to an ester.

It is possible here to add the substances in any sequence. Typically, however, CO is added after the co-reactants have been initially charged in steps a) to e). In addition, CO can also be fed in in two or more steps, in such a way that, for example, a portion of the CO is first fed in, then the mixture is heated, and then a further portion of CO is fed in.

"Reduced pressure" in association with this invention is understood to mean a pressure of 100 mbar or less.

The aluminium triflate can be pretreated, for example, in a reservoir vessel.

The application of reduced pressure can be repeated more than once here.

In one variant of the process, process step c) is conducted at least twice, and the vacuum applied is broken by flooding with inert gas. The inert gas used may, for example, be $N_2$, He or Ar.

The expression $(C_1-C_{12})$-alkyl encompasses straight-chain and branched alkyl groups having 1 to 12 carbon atoms. These are preferably $(C_1-C_8)$-alkyl groups, more preferably $(C_1-C_6)$-alkyl, most preferably $(C_1-C_4)$-alkyl.

The expression $(C_3-C_{20})$-heteroaryl encompasses mono- or polycyclic aromatic hydrocarbon radicals having 3 to 20 carbon atoms, where one or more of the carbon atoms are replaced by heteroatoms. Preferred heteroatoms are N, O and S. The $(C_3-C_{20})$-heteroaryl groups have 3 to 20, preferably 6 to 14 and more preferably 6 to 10 ring atoms. Thus, for example, pyridyl in the context of this invention is a $C_6$-heteroaryl radical; furyl is a $C_5$-heteroaryl radical.

The ethylenically unsaturated compounds used as reactant in the process according to the invention contain one or more carbon-carbon double bonds. These compounds are also referred to as olefins. The double bonds may be terminal or internal.

In one variant of the process, the ethylenically unsaturated compound does not comprise any further functional groups apart from carbon-carbon double bonds.

In the case that the catalyst is formed in situ, the ligand can be added in excess, such that the unbound ligand is also present in the reaction mixture.

In one variant of the process, $R^1$, $R^3$ are each selected from furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl.

In one variant of the process, $R^2$ and $R^4$ are $^{ter}Bu$.

In one variant of the process, the ligand in process step b) has the formula (1):

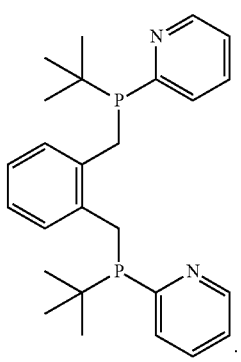

(1)

In one variant of the process, the process comprises the additional process step c'): c') dissolving the pretreated aluminium triflate from c) in a solvent.

The preparing of a solution from the pretreated aluminium triflate makes it possible to feed aluminium triflate continuously into the process without introducing significant amounts of oxygen by entrainment in doing so.

In one variant of the process, the solvent in process step c') is an alcohol.

In one variant of the process, the solvent used in process step c') is the same alcohol as in process step e).

In one variant of the process, the compound in process step b) comprising Pd is selected from palladium dichloride, palladium(II) acetylacetonate, palladium(II) acetate, dichloro(1,5-cyclooctadiene)palladium(II), bis(dibenzylideneacetone)palladium, bis(acetonitrile)dichloropalladium (II), (cinnamyl)palladium dichloride.

Preferably, the compound comprising Pd is $Pd(dba)_2$, $Pd(acac)_2$ or $Pd(OAc)_2$, $Pd(acac)_2$ is particularly suitable.

The mass ratio of Pd to the ethylenically unsaturated compound initially charged in step a) is preferably in the range from 0.001% to 0.5% by weight, preferably from 0.01% to 0.1% by weight, preferably from 0.01% to 0.05% by weight.

The molar ratio of the ligand to Pd is preferably in the range from 0.1:1 to 400:1, preferably from 0.5:1 to 400:1, more preferably from 1:1 to 100:1, most preferably from 2:1 to 50:1.

In one variant of the process, the alcohol in process step e) is selected from methanol, ethanol, 1-propanol, 1-butanol, 1-pentanol, 1-hexanol, 2-propanol, tert-butanol, 3-pentanol, cyclohexanol, phenol, or mixtures thereof.

In one variant of the process, the alcohol in process step e) is methanol.

In one variant of the method, the alcohol in process step e) is used in excess.

In one variant of the method, the alcohol in process step e) is used simultaneously as solvent.

The molar ratio of the ethylenically unsaturated compound initially charged in process step a) to the alcohol added in process step e) is preferably in the range from 1:1 to 1:20, preferably from 1:2 to 1:10, more preferably from 1:3 to 1:6.

In one variant of the process, the ratio of aluminium triflate:ligand in process step d) is in the range from 2.5 mol:1 mol to 15 mol:1 mol.

CO is fed in in process step d) preferably at a partial CO pressure in the range from 0.1 to 10 MPa (1 to 100 bar), preferably in the range from 1 to 5 MPa (10 to 50 bar), more preferably from 1 to 2 MPa (10 to 20 bar).

The reaction mixture is heated in process step g) of the process according to the invention preferably to a temperature in the range from 30° C. to 150° C., preferably from 40 to 140° C., more preferably from 50 to 120° C., in order to convert the ethylenically unsaturated compound to an ester.

The invention is to be described in detail hereinbelow with reference to working examples.

General Procedural Methods

Unless stated otherwise, an argon atmosphere is employed. Reaction vessels have been dried beforehand at high temperature (80° C.) and under oil-pump vacuum.

Liquid substances (e.g. sulfuric acid ($H_2SO_4$)) are degassed by bubbling in argon for at least 15 minutes.

The aluminium triflate ($Al(OTf)_3$) used, and also other solid acids, were pretreated as follows: In the case of a solid acid, this is first weighed out and the vessel is sealed airtight by means of a crimp-fitted septum. By means of a penetrating cannula connected to an argon/reduced pressure distributor station (Schlenk line), this acid is prepared in an oxygen-free manner first by alternately applying reduced pressure (50 mbar) and flooding with argon three times. In addition, argon atmosphere is guaranteed in the subsequent steps, and it is additionally possible to balance the pressure (addition of solutions).

The ligand (1) used is 1,2-bis((tert-butyl(pyridin-2-yl)phosphanyl)methyl)benzere. The precursor used is palladium(II) bis(acetylacetonate) ($Pd(acac)_2$), Di-iso-butene is a mixture consisting of the two C8 isomers 2,4,4-trimethylpent-1-ene and 2,4,4-trimethylpent-2-ene in ratios of about 80:20. 0.5 ml of these samples is spiked with isooctane as internal standard, and conversion and yield are determined by means of GC and GC-MS analysis.

Analysis

GC analysis of diisobutene and 1-octene: For the GC analysis, an Agilent 7890A gas chromatograph having a 30 m HP5 column is used. Temperature profile: 35° C., 10 min; 10° C./min to 200° C.; the injection volume is 1 μl with a split of 50:1.

Experiments

Variation of the Lewis Acids (1-octenes)

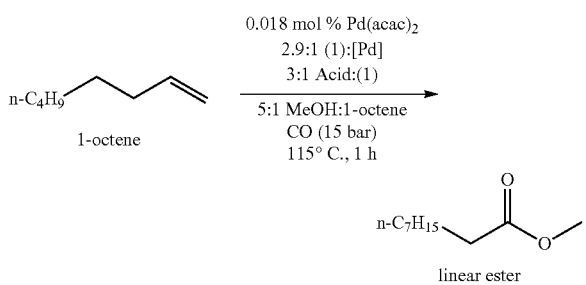

Catalyst Solution:
$Pd(acac)_2$ (8.53 mg) and (1) (35.42 mg) are weighed out in a 10 ml Schlenk vessel and dissolved in methanol (7 ml).
Sulfuric Acid Solution:
$H_2SO_4$ (0.184 mg) is weighed out in a 15 ml Schlenk vessel and dissolved in methanol (10 ml).

The reaction is conducted in 10 ml glass vessels with magnetic stirrer bars. In the case of a solid acid, it is first weighed out (later ratio of acid:(1) should be 3 mol:1 mol) and pretreated as described above. In the case of salicylic acid, for example, 10.76 mg, 0.156 mol %, is weighed out. The amount of catalyst solution required (0.75 ml) is added by means of a μl syringe, so as to result in a starting weight of Pd(acac)$_2$ (0.914 mg, 0.018 mol %) and (1) (3.795 mg, 0.052 mol %). For studies with liquid acids, the amount of acid solution required is added. For example, for an H$_2$SO$_4$ ratio of 3:1, 0.14 ml (0.156 mol %) is added by means of a μl syringe. Finally, methanol is added by means of a syringe, resulting in a total volume of 3.38 ml and a molar MeOH to substrate ratio of 5:1. In the aforementioned example, 2.3 ml is accordingly added. Five of the glass vessels prepared are hung up in a 300 ml autoclave. At the same time, a separate line is guided into each vessel, which enables defined dosage of the substrate at reaction temperature. The autoclave is closed and purged three times with CO, and then CO is injected to 15 bar. The reaction solutions are then heated up to the required temperature of 115° C. After 20 minutes at constant temperature, the substrate is transferred into the reaction vessels (2.6 ml, 16.7 mmol) by means of an HPLC pump. After 1 h, a sample was taken via each substrate line. 0.5 ml of this sample is spiked with isooctane as standard, and yield and n:iso ratios are determined by means of GC and GC-MS analysis.

| Acid | Yield (ester mixture) [%] | n:iso [%] |
| --- | --- | --- |
| H$_2$SO$_4$ | 78 | 68 |
| Al(OTf)$_3$* | 92 | 67 |
| Salicylic acid | 1 | 68 |
| B(OH)$_3$ | 4 | 68 |
| SA (0.156 mol %) [B(OH)$_3$]/[salicylic acid] 1:2 | 4 | 70 |
| SA (0.520 mol %) [B(OH)$_3$]/[salicylic acid] 1:2 | 6 | 70 |
| SA (1.040 mol %) [B(OH)$_3$]/[salicylic acid] 1:2 | 5 | 70 |
| Trimethyl borate | 2 | 68 |
| Methyl borate | 3 | 67 |
| 2-Thienylboronic acid | 2 | 68 |
| Phenylboronic acid | 2 | 68 |
| Tris(pentafluorophenyl)borane | 70 | 67 |
| Ce(SO$_4$)$_2$ | 2 | 67 |

*inventive working examples

Aluminium Triflate Compounds (Diisobutene)

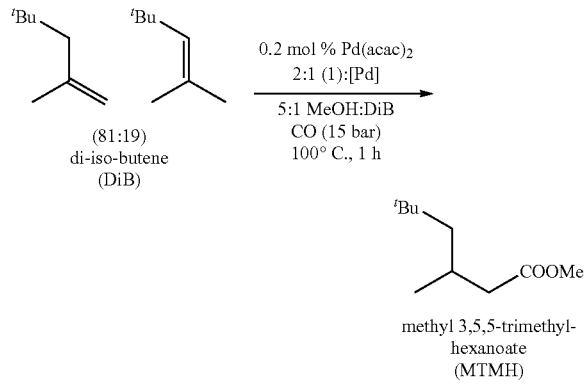

Catalyst Solution:
Pd(acac)$_2$ (83.3 mg) and (1) (238.1 mg) are weighed out in a 10 ml Schlenk vessel and dissolved in methanol (7 ml).

Sulfuric Acid Solution:
H$_2$SO$_4$ (0.386 mg) is weighed out in a 15 ml Schlenk vessel and dissolved in methanol (5 ml).

The reaction is conducted in 10 ml glass vessels with magnetic stirrer bars. In the case of a solid acid, it is first weighed out (4 mol %; molar ratio of acid:(1)=10:1) and pretreated as described above. The amount of catalyst solution required (1 ml) is added by means of a μl syringe, so as to result in a starting weight of Pd(acac)$_2$ (11.9 mg, 0.2 mol %) and (1) (34.01 mg, 0.4 mol %). For studies with the liquid acid H$_2$SO$_4$, the amount of acid solution required, 1 ml (4 mol %), is added by means of a pi syringe. Finally, methanol is added by means of a μl syringe, resulting in a total volume of 3.94 ml and a molar MeOH to substrate ratio of 5:1. Five of the glass vessels prepared are hung up in a 300 ml autoclave. At the same time, a separate line is guided into each vessel, which enables defined dosage of the substrate (3 ml, 19.4 mmol) at reaction temperature. The autoclave is closed and purged three times with CO, and then CO is injected to 15 bar. The reaction solutions are then heated up to the required temperature of 115° C. After 20 minutes at constant temperature, the substrate is transferred into the reaction vessels (3 ml, 19.4 mmol) by means of an HPLC pump. After 1 h, a sample was taken via each substrate line. 0.5 ml of this sample is spiked with isooctane as standard, and yield and n:iso ratios are determined by means of GC and GC-MS analysis.

| Acid | Yield (MTMH) [%] |
| --- | --- |
| H$_2$SO$_4$ | 87 |
| Al(OTf)$_3$* | 94 |
| Cu(OTf)$_3$ | <1 |
| Fe(OTf)$_3$ | <1 |
| Mg(OTf)$_3$ | <1 |
| Na(OTf)$_3$ | <1 |
| Zn(OTf)$_3$ | <1 |
| Al(H$_2$PO$_4$)$_3$ | 3 |
| Al$_2$(SO$_4$)$_3$ | 8 |
| Al(acac)$_3$ | <1 |

*inventive working examples

Variation of the Ligand (1-octenes)

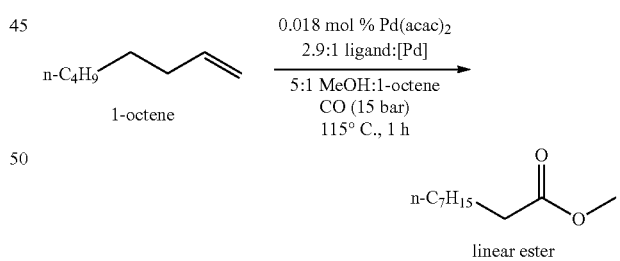

Catalyst Solution:
Pd(acac)$_2$ (0.004 mol/l) and (ligand) (0.0116 mol/l) are weighed out in a 10 ml Schlenk vessel for 7 ml of methanol solution.

The reaction is conducted in 10 ml glass vessels with magnetic stirrer bars. In the case of a solid acid, it is first weighed out and pretreated as described above. In the example of the required ratio of 1 mol:1 mol, 4.13 mg Al(OTf)$_3$ is weighed out. The amount of catalyst solution required (0.75 ml) is added by means of a μl syringe, so as to result in a starting weight of Pd(acac)$_2$ (0.914 mg, 0.018 mol %) and (1) (3.795 mg, 0.052 mol %). Finally, methanol is added by means of a syringe, resulting in a total volume of 3.38 ml and a molar MeOH to substrate ratio of 5:1. Five of the glass vessels prepared are hung up in a 300 ml autoclave. At the same time, a separate line is guided into each vessel, which enables defined dosage of the substrate at reaction temperature. The autoclave is closed and purged three times with CO, and then CO is injected to 15 bar. The reaction solutions are then heated up to the required temperature of 115° C. After 20 minutes at constant temperature, the substrate is transferred into the reaction vessels (2.6 ml, 16.7 mmol) by means of an HPLC pump. After 1 h, a sample was taken via each substrate line. 0.5 ml of this sample is spiked with isooctane as standard, and yield and n:iso ratios are determined by means of GC and GC-MS analysis.

| Ligand | Acid:ligand [mol]:[mol] | Yield (ester mixture) [%] | n:iso [%] |
|---|---|---|---|
| L1 | 0.5:1 | 70 | 68 |
|  | 1:1 | 82 | 68 |
|  | 3:1* | 92 | 68 |
|  | 5:1* | 89 | 68 |
|  | 7:1* | 88 | 68 |
|  | 10:1 | 88 | 68 |
| L2 | 3:1 | 19 | 92 |
|  | 5:1 | 17 | 92 |
|  | 10:1 | 15 | 92 |
|  | 15:1 | 17 | 92 |
| L3 | 1:1 | 9 | 72 |
|  | 3:1 | 10 | 72 |
|  | 5:1 | 10 | 72 |
|  | 7.5:1 | 11 | 72 |
| L4 | 1:1 | 54 | 69 |
|  | 3:1 | 65 | 67 |
|  | 5:1 | 76 | 68 |
|  | 7.5:1 | 76 | 68 |

*inventive working examples

Variation of the Acid Equivalents (1-octanes)

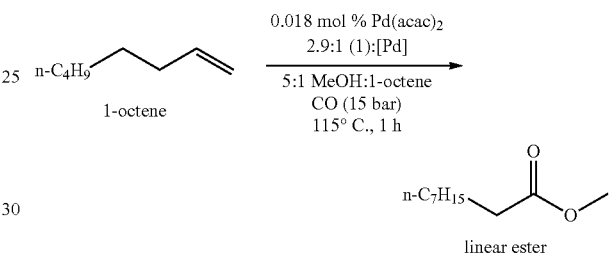

Catalyst Solution:

Pd(acac)$_2$ (8.53 mg) and (1) (35.42 mg) are weighed out in a 10 ml Schlenk vessel and dissolved in methanol (7 ml).

Sulfuric Acid Solution:

H$_2$SO$_4$ (0.184 mg) is weighed out in a 15 ml Schlenk vessel and dissolved in methanol (10 ml).

The reaction is conducted in 10 ml glass vessels with magnetic stirrer bars. In the case of a solid acid, it is first weighed out and pretreated as described above. The amount of catalyst solution required (0.75 ml) is added by means of a μl syringe, so as to result in a starting weight of Pd(acac)$_2$ (0.914 mg, 0.018 mol %) and (1) (3.795 mg, 0.052 mol %). For studies with liquid acids, the amount of acid solution required is added. For example, for an H$_2$SO$_4$ ratio of 4:1, 0.19 ml (0.21 mol %) is added by means of a μl syringe. Finally, methanol is added by means of a syringe, resulting in a total volume of 3.38 ml and a molar MeOH to substrate ratio of 5:1. In the aforementioned example, 2.44 ml is accordingly added. Five of the glass vessels prepared are hung up in a 300 ml autoclave. At the same time, a separate line is guided into each vessel, which enables defined dosage of the substrate at reaction temperature. The autoclave is closed and purged three times with CO, and then CO is injected to 15 bar. The reaction solutions are then heated up to the required temperature of 115° C. After 20 minutes at constant temperature, the substrate is transferred into the reaction vessels (2.6 ml, 16.7 mmol) by means of an HPLC pump. After 1 h, a sample was taken via each substrate line. 0.5 ml of this sample is spiked with isooctane as standard, and yield and n:iso ratios are determined by means of GC and GC-MS analysis.

| Acid | Acid:(1) [mol:mol] | Yield (ester mixture) [%] |
|---|---|---|
| $H_2SO_4$ | 1:1 | 44 |
|  | 2:1 | 73 |
|  | 3:1 | 78 |
|  | 4:1 | 73 |
|  | 5:1 | 65 |
|  | 7:1 | 48 |
|  | 10:1 | 34 |
| Al(OTf)$_3$ | 1:1 | 82 |
|  | 3:1* | 92 |
|  | 5:1* | 89 |
|  | 7:1* | 88 |
|  | 10:1* | 88 |

*inventive working examples

Variation of the Acid Equivalents (Diisobutene)

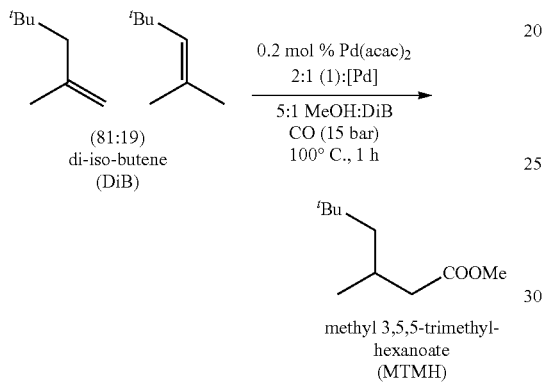

(81:19) di-iso-butene (DiB)

0.2 mol % Pd(acac)$_2$
2:1 (1):[Pd]
5:1 MeOH:DiB
CO (15 bar)
100° C., 1 h methyl 3,5,5-trimethyl-hexanoate (MTMH)

Catalyst Solution:

Pd(acac)$_2$ (83.3 mg) and (1) (238.1 mg) are weighed out in a 10 ml Schlenk vessel and dissolved in methanol (7 ml)

Sulfuric Acid Solution:

$H_2SO_4$ (0.386 mg) is weighed out in a 15 ml Schlenk vessel and dissolved in methanol (5 ml).

The reaction is conducted in 10 ml glass vessels with magnetic stirrer bars. In the case of a solid acid, it is first weighed out and pretreated as described above. The amount of catalyst solution required (1 ml) is added by means of a μl syringe, so as to result in a starting weight of Pd(acac)$_2$ (11.9 mg, 0.2 mol %) and (1) (34.01 mg, 0.4 mol %). For studies with liquid acids, the amount of acid solution required is added. For example, for an $H_2SO_4$ ratio of 1:1, 0.1 ml (0.4 mol %) is added by means of a pi syringe. Finally, methanol is added by means of a syringe, resulting in a total volume of 3.94 ml and a molar MeOH to substrate ratio of 5:1. In the aforementioned example, 2.8 ml is accordingly added. Five of the glass vessels prepared are hung up in a 300 ml autoclave. At the same time, a separate line is guided into each vessel, which enables defined dosage of the substrate (3 ml, 19.4 mmol) at reaction temperature. The autoclave is closed and purged three times with CO, and then CO is injected to 15 bar. The reaction solutions are then heated up to the required temperature of 115° C. After 20 minutes at constant temperature, the substrate is transferred into the reaction vessels (3 ml, 19.4 mmol) by means of an HPLC pump. After 1 h, a sample was taken via each substrate line. 0.5 ml of this sample is spiked with isooctane as standard, and yield and n:iso ratios are determined by means of GC and GC-MS analysis.

| Acid | Acid:(1) [mol:mol] | Yield (MTMH) [%] |
|---|---|---|
| $H_2SO_4$ | 1 | 80 |
|  | 2.5 | 88 |
|  | 4 | 91 |
|  | 7 | 89 |
|  | 10 | 87 |
|  | 13 | 81 |
|  | 15 | 70 |
| Al(OTf)$_3$ | 1 | 84 |
|  | 2.5:1* | 92 |
|  | 4:1* | 92 |
|  | 7:1* | 95 |
|  | 10:1* | 94 |
|  | 13:1* | 92 |
|  | 15:1* | 93 |

*inventive working examples

The invention claimed is:

1. Process comprising the process steps of:
   a) initially charging an ethylenically unsaturated compound,
   b) adding a ligand of formula (I):

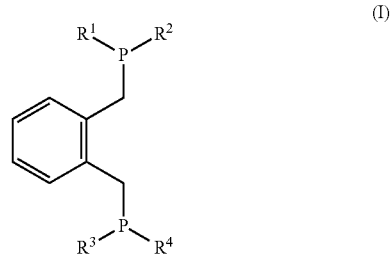

where
   $R^1$ and $R^3$ are each a —($C_3$-$C_{20}$)-heteroaryl radical,
   $R^2$ and $R^4$ are each —($C_1$-$C_{12}$)-alkyl,
   and a compound comprising Pd;
   c) pretreating aluminium triflate at least twice by applying a vacuum to reduce pressure and the vacuum applied is broken by flooding with inert gas;
   d) adding the pretreated aluminium triflate from c) as a solution, where the ratio of aluminium triflate:ligand is in the range from 2.5 mol:1 mol to 15 mol:1 mol;
   e) adding an alcohol;
   f) feeding in CO;
   g) heating the reaction mixture from a) to f), with conversion of the ethylenically unsaturated compound to an ester.

2. Process according to claim 1,
   where $R^1$, $R^3$ are each selected from furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl.

3. Process according to claim 1,
   where $R^2$ and $R^4$ are $^{ter}$Bu.

4. Process according to claim 1,
wherein the ligand in process step b) has the formula (1):

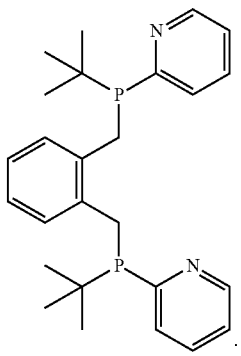
(1)

5. Process according to claim 1,
wherein the process comprises the additional process step c'):

c') dissolving the pretreated aluminium triflate from c) in a solvent.

6. Process according to claim 5,
wherein the solvent used in process step c') is the same alcohol as in process step e).

7. Process according to claim 1,
wherein the compound in process step b) comprising Pd is selected from palladium dichloride, palladium(II) acetylacetonate, palladium(II) acetate, dichloro(1,5-cyclooctadiene) palladium(II), bis(dibenzylideneacetone) palladium, bis(acetonitrile)dichloropalladium(II), (cinnamyl)palladium dichloride.

8. Process according to claim 1,
wherein the alcohol in process step e) is selected from methanol, ethanol, 1-propanol, 1-butanol, 1-pentanol, 1-hexanol, 2-propanol, tart-butanol, 3-pentanol, cyclohexane, phenol, or mixtures thereof.

9. Process according to claim 1,
wherein the alcohol in process step e) is methanol.

* * * * *